(12) United States Patent
Kang et al.

(10) Patent No.: US 12,226,753 B2
(45) Date of Patent: Feb. 18, 2025

(54) AMMOXIDATION CATALYST FOR PROPYLENE, MANUFACTURING METHOD OF THE SAME CATALYST, AMMOXIDATION METHOD USING THE SAME CATALYST

(71) Applicant: LG CHEM, LTD., Seoul (KR)

(72) Inventors: Kyungyeon Kang, Daejeon (KR); Ji Yeon Kim, Daejeon (KR); Jun Seon Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 737 days.

(21) Appl. No.: 17/296,529

(22) PCT Filed: Sep. 25, 2020

(86) PCT No.: PCT/KR2020/013097
§ 371 (c)(1),
(2) Date: May 24, 2021

(87) PCT Pub. No.: WO2021/066409
PCT Pub. Date: Apr. 8, 2021

(65) Prior Publication Data
US 2022/0023837 A1   Jan. 27, 2022

(30) Foreign Application Priority Data

Sep. 30, 2019 (KR) .................. 10-2019-0121172
Oct. 25, 2019 (KR) .................. 10-2019-0134088
Sep. 24, 2020 (KR) .................. 10-2020-0123875

(51) Int. Cl.
*B01J 21/08* (2006.01)
*B01J 23/00* (2006.01)
(Continued)

(52) U.S. Cl.
CPC ......... *B01J 23/002* (2013.01); *B01J 23/8876* (2013.01); *B01J 35/613* (2024.01);
(Continued)

(58) Field of Classification Search
CPC .......... B01J 21/08; B01J 23/002; B01J 23/02; B01J 23/04; B01J 23/18; B01J 23/22;
(Continued)

(56) References Cited

U.S. PATENT DOCUMENTS 3,766,092 A   10/1973 Hirakawa et al.
4,052,332 A   10/1977 D'Amore et al.
(Continued)

FOREIGN PATENT DOCUMENTS

CA   805705 A    2/1969
CN   1744949 A   3/2006
(Continued)

OTHER PUBLICATIONS

Binh et al., "Ammoxidation of Acrolein to Acrylonitrile Over Bismuth Molybdate Catalysts", Applied Catalysis a General, vol. 520 (2016), pp. 7-12.
(Continued)

*Primary Examiner* — Cam N. Nguyen
(74) *Attorney, Agent, or Firm* — BRYAN CAVE LEIGHTON PAISNER LLP (57) ABSTRACT

An ammoxidation catalyst includes a metal oxide represented by Chemical Formula 1 supported on a silica carrier, wherein the catalyst has pores having a diameter of 5 to 200 nm, a pore volume of 0.1 to 3.0 cm³/g, and a BET surface area of 50 m2/g to 1,000 m2/g:

$$Mo_{12}Bi_aFe_bA_cB_dC_eO_x \qquad \text{Chemical Formula 1}$$

(Continued)

wherein in Chemical Formula 1,
A is one or more elements of Ni, Mn, Co, Zn, Mg, Ca, and Ba,
B is one or more elements of Li, Na, K, Rb, and Cs,
C is one or more elements of Cr, W, B, Al, Ca, and V, and
a to e, and x are respectively fractions of each atom or atomic group, wherein a is 0.1 to 5, b is 0.1 to 5, c is 0.1 to 10, d is 0.1 to 2, e is 0 to 10, and x is 24 to 48.

20 Claims, 2 Drawing Sheets

(51) Int. Cl.
| | | |
|---|---|---|
| *B01J 23/02* | (2006.01) | |
| *B01J 23/04* | (2006.01) | |
| *B01J 23/18* | (2006.01) | |
| *B01J 23/22* | (2006.01) | |
| *B01J 23/26* | (2006.01) | |
| *B01J 23/28* | (2006.01) | |
| *B01J 23/30* | (2006.01) | |
| *B01J 23/31* | (2006.01) | |
| *B01J 23/34* | (2006.01) | |
| *B01J 23/74* | (2006.01) | |
| *B01J 23/745* | (2006.01) | |
| *B01J 23/75* | (2006.01) | |
| *B01J 23/755* | (2006.01) | |
| *B01J 23/78* | (2006.01) | |
| *B01J 23/84* | (2006.01) | |
| *B01J 23/843* | (2006.01) | |
| *B01J 23/847* | (2006.01) | |
| *B01J 23/85* | (2006.01) | |
| *B01J 23/88* | (2006.01) | |
| *B01J 23/881* | (2006.01) | |
| *B01J 23/887* | (2006.01) | |
| *B01J 35/10* | (2006.01) | |
| *B01J 35/61* | (2024.01) | |
| *B01J 35/63* | (2024.01) | |
| *B01J 35/64* | (2024.01) | |
| *B01J 37/02* | (2006.01) | |
| *B01J 37/04* | (2006.01) | |
| *B01J 37/08* | (2006.01) | |
| *C07C 253/26* | (2006.01) | |

(52) U.S. Cl.
CPC ........... *B01J 35/615* (2024.01); *B01J 35/635* (2024.01); *B01J 35/638* (2024.01); *B01J 35/647* (2024.01); *B01J 37/0209* (2013.01); *B01J 37/04* (2013.01); *B01J 37/08* (2013.01); *C07C 253/26* (2013.01); *B01J 21/08* (2013.01)

(58) Field of Classification Search
CPC ............ B01J 23/26; B01J 23/28; B01J 23/30; B01J 23/31; B01J 23/34; B01J 23/74; B01J 23/745; B01J 23/75; B01J 23/755; B01J 23/78; B01J 23/84; B01J 23/8437; B01J 23/8472; B01J 23/85; B01J 23/88; B01J 23/881; B01J 23/8872; B01J 35/1014; B01J 35/1019; B01J 35/1042; B01J 35/1047; B01J 37/1061; B01J 37/0209; B01J 37/04; B01J 37/08
See application file for complete search history.

(56) References Cited

U.S. PATENT DOCUMENTS

| | | | | |
|---|---|---|---|---|
| 4,123,453 A * | 10/1978 | Grasselli | ............... | C07C 253/26 502/311 |
| 4,156,660 A * | 5/1979 | Grasselli | ............... | C07C 253/26 502/212 |
| 4,176,234 A * | 11/1979 | Grasselli | ............... | C07C 51/252 558/324 |
| 4,182,907 A * | 1/1980 | Grasselli | ............... | B01J 23/8876 568/480 |
| 4,259,211 A * | 3/1981 | Krabetz | ............... | B01J 23/34 502/178 |
| 4,264,476 A | 4/1981 | Umemura et al. | | |
| 4,280,929 A * | 7/1981 | Shaw | ............... | B01J 23/28 502/232 |
| 4,290,922 A | 9/1981 | Umemura et al. | | |
| 4,298,763 A * | 11/1981 | Engelbach | ............ | B01J 23/8877 16/365 |
| 4,374,759 A | 2/1983 | Khoobiar | | |
| 4,382,880 A * | 5/1983 | Derrien | ............... | B01J 23/8878 502/313 |
| 4,388,223 A | 6/1983 | Ferlazzo et al. | | |
| 4,388,226 A * | 6/1983 | Derrien | ............... | B01J 23/002 502/308 |
| 4,418,007 A * | 11/1983 | Derrien | ............... | B01J 37/031 502/316 |
| 4,479,013 A | 10/1984 | Khoobiar | | |
| 4,503,001 A * | 3/1985 | Grasselli | ............... | B01J 27/186 558/324 |
| 4,541,964 A * | 9/1985 | Katsumata | ............ | C07C 253/26 558/324 |
| 4,590,173 A | 5/1986 | Sasaki et al. | | |
| 4,609,635 A | 9/1986 | Canavesi et al. | | |
| 4,767,878 A * | 8/1988 | Grasselli | ............... | B01J 27/192 558/324 |
| 4,863,891 A * | 9/1989 | Grasselli | ............... | B01J 27/192 502/212 |
| 5,093,299 A | 3/1992 | Suresh et al. | | |
| 5,175,334 A | 12/1992 | Suresh et al. | | |
| 5,212,137 A | 5/1993 | Suresh et al. | | |
| 5,602,280 A | 2/1997 | Nagai et al. | | |
| 5,663,113 A | 9/1997 | Midorikawa et al. | | |
| 5,728,894 A * | 3/1998 | Nagano | ............... | B01J 35/1066 502/305 |
| 5,780,664 A | 7/1998 | Aoki | | |
| 6,143,690 A | 11/2000 | Komada et al. | | |
| 6,245,931 B1 | 6/2001 | Aoki et al. | | |
| 6,458,742 B1 | 10/2002 | Paparizos et al. | | |
| 6,509,508 B2 * | 1/2003 | Kimura | ............... | C07C 51/235 562/537 |
| 6,525,217 B1 * | 2/2003 | Unverricht | ............ | B01J 23/002 562/544 |
| 6,545,177 B2 * | 4/2003 | Tanimoto | ............ | C07C 51/252 502/309 |
| 6,723,869 B1 | 4/2004 | Mori et al. | | |
| 6,781,013 B2 * | 8/2004 | Tanimoto | ............ | B01J 23/8885 562/544 |
| 6,784,134 B2 * | 8/2004 | Kasuga | ............... | C07C 45/35 562/532 |
| 6,797,839 B1 * | 9/2004 | Hibst | ............... | C01G 39/006 502/313 |
| 6,818,702 B1 * | 11/2004 | Orikabe | ............... | H01L 23/293 525/122 |
| 6,878,847 B2 * | 4/2005 | Kasuga | ............... | B01J 23/31 502/313 |
| 6,888,024 B2 * | 5/2005 | Dieterle | ............... | B01J 23/002 562/546 |
| 6,921,836 B1 * | 7/2005 | Hibst | ............... | B01J 23/002 502/312 |
| 6,965,046 B2 | 11/2005 | Paparizos et al. | | |
| 7,071,140 B2 | 7/2006 | Paparizos et al. | | |
| 7,348,291 B2 | 3/2008 | Paparizos et al. | | |
| 7,365,041 B2 | 4/2008 | Miyaki et al. | | |
| 7,473,666 B2 | 1/2009 | Yanagi et al. | | |
| 7,579,501 B2 | 8/2009 | Teshigahara et al. | | |
| 7,632,777 B2 | 12/2009 | Teshigahara et al. | | |
| 7,635,786 B2 * | 12/2009 | Shin | ............... | B01J 23/002 562/533 |
| 7,638,458 B2 * | 12/2009 | Shin | ............... | B01J 27/0576 502/215 |
| 7,649,111 B2 | 1/2010 | Liang et al. | | |
| 7,732,367 B2 | 6/2010 | Stevenson et al. | | |

(56) References Cited

U.S. PATENT DOCUMENTS

| | | | |
|---|---|---|---|
| 7,943,710 B2* | 5/2011 | Shin | B01J 23/002 526/101 |
| 7,999,133 B2 | 8/2011 | Stevenson et al. | |
| 8,153,546 B2 | 4/2012 | Brazdil et al. | |
| 8,247,344 B2* | 8/2012 | Shin | B01J 23/8877 562/546 |
| 8,258,073 B2 | 9/2012 | Besecker et al. | |
| 8,350,075 B2 | 1/2013 | Brazdil et al. | |
| 8,354,482 B2* | 1/2013 | Shin | B01J 35/0006 526/64 |
| 8,361,923 B2 | 1/2013 | Kano et al. | |
| 8,420,566 B2* | 4/2013 | Brazdil | C07C 253/26 558/324 |
| 8,455,388 B2 | 6/2013 | Brazdil et al. | |
| 8,686,194 B2 | 4/2014 | Macht et al. | |
| 9,199,921 B2 | 12/2015 | Endo et al. | |
| 9,211,527 B1 | 12/2015 | Brazdil et al. | |
| 9,346,036 B2 | 5/2016 | Yoshida et al. | |
| 9,358,528 B2 | 6/2016 | Brazdil et al. | |
| 9,364,817 B2 | 6/2016 | Yoshida et al. | |
| 9,815,045 B2 | 11/2017 | Lugmair et al. | |
| 9,844,769 B2 | 12/2017 | Brazdil et al. | |
| 10,137,437 B2 | 11/2018 | Sokolovskii et al. | |
| 10,479,759 B2 | 11/2019 | Li et al. | |
| 10,479,760 B2 | 11/2019 | Lugmair et al. | |
| 10,626,082 B2 | 4/2020 | Brazdil et al. | |
| 10,682,631 B2 | 6/2020 | Amakawa et al. | |
| 10,780,427 B2 | 9/2020 | Brazdil et al. | |
| 10,894,247 B2 | 1/2021 | Yang et al. | |
| 10,940,463 B2 | 3/2021 | Iitsuka et al. | |
| 11,433,383 B2 | 9/2022 | Aiki et al. | |
| 2001/0051589 A1 | 12/2001 | Van Berge et al. | |
| 2002/0198398 A1 | 12/2002 | Paparizos et al. | |
| 2004/0063988 A1 | 4/2004 | Hechler et al. | |
| 2005/0187406 A1 | 8/2005 | Kang et al. | |
| 2005/0245623 A1 | 11/2005 | Van Berge et al. | |
| 2006/0155139 A1 | 7/2006 | Yanagi et al. | |
| 2006/0199730 A1 | 9/2006 | Seely et al. | |
| 2010/0076208 A1 | 3/2010 | Dhingra et al. | |
| 2011/0092757 A1 | 4/2011 | Akagishi et al. | |
| 2011/0237753 A1 | 9/2011 | Brazdil et al. | |
| 2012/0130112 A1 | 5/2012 | Brazdil et al. | |
| 2013/0023699 A1 | 1/2013 | Macht et al. | |
| 2015/0238939 A1 | 8/2015 | Yoshida et al. | |
| 2015/0367329 A1* | 12/2015 | Lim | B01J 23/8876 562/546 |
| 2016/0051967 A1 | 2/2016 | Sokolovskii et al. | |
| 2016/0175817 A1 | 6/2016 | Brazdil et al. | |
| 2017/0114007 A1 | 4/2017 | Brazdil et al. | |
| 2018/0133699 A1 | 5/2018 | Brazdil et al. | |
| 2018/0222850 A1 | 8/2018 | Li et al. | |
| 2018/0222851 A1 | 8/2018 | Lugmair et al. | |
| 2018/0318803 A1 | 11/2018 | Fukuzawa et al. | |
| 2019/0001309 A1 | 1/2019 | Fukuzawa et al. | |
| 2019/0076829 A1* | 3/2019 | Sprenger | B01J 27/057 |
| 2021/0070693 A1 | 3/2021 | Morii et al. | |
| 2022/0001361 A1 | 1/2022 | Kim et al. | |
| 2022/0002233 A1 | 1/2022 | Kang et al. | |
| 2022/0023837 A1 | 9/2022 | Kang et al. | |
| 2022/0395817 A1 | 12/2022 | Kim et al. | |
| 2023/0373908 A1 | 11/2023 | Ryou et al. | |

FOREIGN PATENT DOCUMENTS

| | | | |
|---|---|---|---|
| CN | 110214054 A | 9/2019 | |
| CN | 110248730 A | 9/2019 | |
| EP | 1 602 405 A1 * | 12/2005 | B01J 23/88 |
| EP | 3974058 A1 | 3/2022 | |
| JP | S47013313 U | 10/1972 | |
| JP | S55056839 A | 4/1980 | |
| JP | S57171437 A | 10/1982 | |
| JP | S60-166037 A | 8/1985 | |
| JP | H0747271 A | 2/1995 | |
| JP | 2000037631 A | 2/2000 | |
| JP | 2002526241 A | 8/2002 | |
| JP | 2006521916 A | 9/2006 | |
| JP | 2010240593 A | 10/2010 | |
| JP | 2005313167 A | 8/2011 | |
| JP | 2013527141 A | 6/2013 | |
| JP | 2013169482 A | 9/2013 | |
| JP | 2016120468 A | 7/2016 | |
| JP | 2016520418 A | 7/2016 | |
| JP | 6124883 B2 | 5/2017 | |
| JP | 2018-140326 A | 9/2018 | |
| JP | 2022512791 A | 2/2022 | |
| KR | 1020050098270 A | 10/2005 | |
| KR | 10-0687671 B1 | 3/2007 | |
| KR | 10-0977358 B1 | 8/2010 | |
| KR | 10-2012-0021858 A | 3/2012 | |
| KR | 10-2013-007625 A | 1/2013 | |
| KR | 10-2015-0046224 A | 4/2015 | |
| KR | 10-1537459 B1 | 7/2015 | |
| KR | 10-2016-0066922 A | 6/2016 | |
| KR | 10-206-0083698 A | 7/2016 | |
| KR | 10-2017-0007947 A | 1/2017 | |
| KR | 10-2017-0139602 A | 12/2017 | |
| WO | 2004078344 A1 | 9/2004 | |
| WO | 2011-119203 A1 | 9/2011 | |
| WO | 2014169163 | 10/2014 | |
| WO | 2014051090 A1 | 8/2016 | |
| WO | 2017130909 A1 | 8/2017 | |
| WO | 2018148158 A1 | 8/2018 | |
| WO | 2018148240 A1 | 8/2018 | |
| WO | 2019187786 A1 | 10/2019 | |

OTHER PUBLICATIONS

Industrial Catalysis, Wang Wenxing et al., Beijing: Chemical Industry Press, p. 223, Dec. 1978.

\* cited by examiner

AMMOXIDATION CATALYST FOR PROPYLENE, MANUFACTURING METHOD OF THE SAME CATALYST, AMMOXIDATION METHOD USING THE SAME CATALYST

The present application is a National Phase entry pursuant to 35 U.S.C. § 371 of International Application No. PCT/KR2020/013097 filed on Sep. 25, 2020, and claims priority to and the benefit of Korean Patent Application No. 10-2019-0121172 filed on Sep. 30, 2019, Korean Patent Application No. 10-2019-0134088 filed on Oct. 25, 2019, and Korean Patent Application No. 10-2020-0123875 filed on Sep. 24, 2020 with the Korean Intellectual Property Office, the disclosures of which are herein incorporated by reference in their entirety.

FIELD

This invention relates to an ammoxidation catalyst for propylene, a manufacturing method of the same, and an ammoxidation method using the same.

BACKGROUND

An ammoxidation process of propylene is based on a mechanism of reduction in which ammonia and propylene are reacted and reoxidized, and in order to increase conversion of the reactant (namely, propylene), selectivity and yield of the reaction product (namely acrylonitrile), catalysts of various compositions have been studied.

Specifically, since a Mo(molybdenum)-Bi(bismuth) oxide catalyst has been suggested, in order to increase the catalytic activity and stability, catalysts to which metals of various oxidation states are added have been studied. As the result, the yield of acrylonitrile was improved compared to the initial studies, according to the kind or amount of added metals.

However, despite diversification of catalyst compositions, due to insufficient studies on the structure and properties, remarkable increase in the conversion of the reactant (namely, propylene) and selectivity of the reaction product (namely, acrylonitrile) during the ammoxidation of propylene was limited.

Specifically, in general, metal precursors of aimed compositions and nano silica sol are coprecipitated, and then, spray dried and calcined, thus obtaining a catalyst of a secondary particle structure in which metal oxide particles and silica particles are agglomerated.

More specifically, in the catalyst of a secondary particle structure, metal oxide particles are uniformly distributed inside and outside, but internal pores are scarcely included, and thus, parts capable of participating in ammoxidation of propylene are limited to the external surface parts.

It is an object of the invention to provide an ammoxidation catalyst for propylene in which not only the external surface part (namely, the surface of a catalyst) but also the internal surfaces (pores) can participate in reactions, and to prepare acrylonitrile with higher yield by using such a catalyst.

SUMMARY

Specifically, according to one embodiment of the invention, there is provided an ammoxidation catalyst for propylene having a structure wherein metal oxide of a specific composition is supported in a silica carrier, and having large pore size and volume and wide BET specific surface area in the supported state.

The catalyst of one embodiment has wide effective surface area capable of participating in reactions, and thus, has high catalytic efficiency and reactivity.

Thus, using the catalyst of one embodiment, propylene can be converted with higher rate, and acrylonitrile can be prepared with higher selectivity and yield.

DETAILED DESCRIPTION

Although various modifications can be made to the invention and the invention may have various forms, specific examples will be illustrated and explained in detail below. However, it should be understood that these are not intended to limit the invention to specific disclosure, and that the invention includes all modifications, equivalents or replacements thereof without departing from the spirit and technical scope of the invention. In explanation of the invention, in case it is judged that specific explanations regarding related known technologies may obscure the subject matter of the invention, those explanations will be omitted.

And, terms including ordinal numbers such as "a first", "a second" and the like are used to explain various constructional elements, but the constructional elements are not limited by these terms. These terms are used only to distinguish one constructional element from other constructional elements. For example, the first constructional element may be named as the second constructional element, and similarly, the second constructional elements may be also named as the first constructional elements, without departing from the scope of the right of the invention.

A singular expression includes a plural expression thereof, unless it is expressly stated or obvious from the context that such is not intended. As used herein, the terms "comprise" or "have", etc. are intended to designate the existence of practiced characteristic, number, step, constructional element or combinations thereof, and they are not intended to preclude the possibility of existence or addition of one or more other characteristics, numbers, steps, constructional elements or combinations thereof.

Hereinafter, "particle diameter Dv" means a particle diameter at v % point in cumulative volume distribution according to particle diameter. Namely, D50 is a particle diameter at 50% point in cumulative volume distribution according to particle diameter, D90 is a particle diameter at 90% point in the cumulative volume distribution according to particle diameter, and D10 is a particle diameter at 10% point in cumulative volume distribution according to particle diameter.

The Dv may be measured using a laser diffraction method. Specifically, particle size distribution is calculated by dispersing powders to be measured in a dispersion medium, and then, introducing them in a commercially available laser diffraction particle size measuring device (for example, Micritrac S3500), and measuring diffraction pattern difference according to particle size when particles pass through laser beam. By calculating particle diameter at 10%, 50% and 90% points in cumulative volume distribution according to particle diameter, D10, D50 an D90 can be measured.

Hereinafter, an ammoxidation catalyst for propylene according to one embodiment will be explained in detail with reference to drawings.

An Ammoxidation Catalyst for Propylene

According to one embodiment of the invention, there is provided an ammoxidation catalyst for propylene in which metal oxide represented by the following Chemical Formula 1 is supported on a silica carrier, wherein the catalyst comprises pores having a diameter of 5 to 200 nm and volume of 0.1 to 3.0 cm³/g, and has BET specific surface area of 50 m²/g to 1000 m²/g:

$$Mo_{12}Bi_aFe_bA_cB_dC_eO_x$$  Chemical Formula 1 in the Chemical Formula 1,

A is one or more elements of Ni, Mn, Co, Zn, Mg, Ca, and Ba,

B is one or more elements of Li, Na, K, Rb, and Cs,

C is one or more elements of Cr, W, B, Al, Ca, and V, and a to e, and x are respectively fractions of each atom or atomic group, and a is 0.1 to 5, b is 0.1 to 5, c is 0.01 to 10, d is 0.01 to 2, e is 0 to 10, and x is 24 to 48

Figure 1:
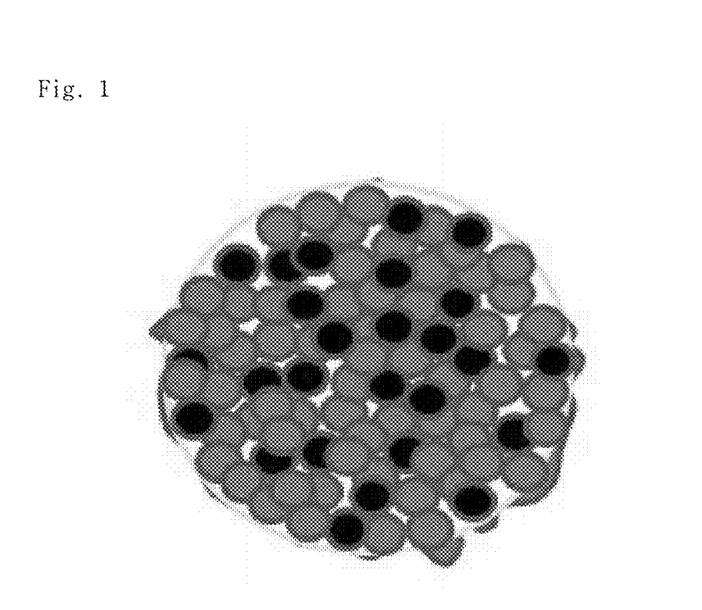
FIG. 1 is a schematic illustration showing the catalyst prepared using coprecipitation and spray drying.

Commonly known propylene ammoxidation catalysts are prepared by coprecipitation and spray drying, and provided as a secondary particle structure in which metal oxide nanoparticles and silica nanoparticles are agglomerated (FIG. 1).

Since metal oxide particles are uniformly distributed inside and outside, but parts capable of participating in propylene ammoxidation reactions are limited to the external surface parts (namely, the surfaces of secondary particles), and a small surface area is provided, the amount of ammonia detached from the catalyst surface during the propylene ammoxidation reaction is large.

Figure 2:
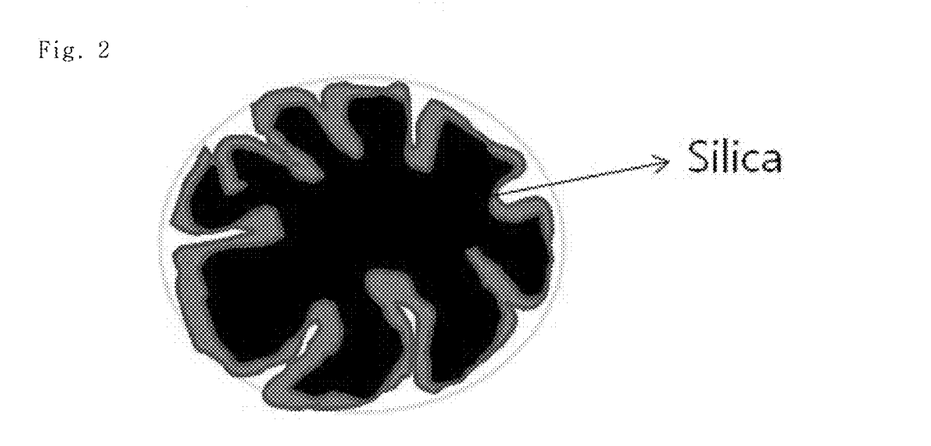
FIG. 2 is a schematic illustration showing the catalyst according to one embodiment.

On the contrary, since the catalyst of one embodiment is prepared by impregnation, it may be provided as a structure wherein metal oxide is supported in a silica carrier (FIG. 2).

For example, a silica carrier may be impregnated in a metal precursor solution by immersing the silica carrier in the metal precursor solution prepared such that stoichiometric mole ratio of metal oxide aimed is satisfied.

Thereafter, if a solvent (namely, water) is removed by drying, the metal precursor may remain on the pore walls of the silica carrier, and the metal precursor may be oxidized during a calcination process to form a film continuously coating the pore walls of the silica carrier.

The catalyst of one embodiment thus prepared, even if a classification process is not progressed as post treatment after preparation, may have smaller fine powder content and improved durability relative to a catalyst prepared with the same composition by coprecipitation and spray drying.

And, by controlling the composition of the metal oxide so as to further include metals forming active sites for a propylene ammoxidation reaction, as well as Mo and Bi known to increase the activity of an ammoxidation reaction, the catalytic activity may be further increased.

Particularly, in the catalyst of one embodiment, by uniformly supporting the metal oxide in the internal pores of the silica carrier, parts capable of participating in a propylene ammoxidation reaction may be extended to the internal surfaces (pores) as well as to the external surface parts (namely, the surface of the catalyst).

Specifically, the catalyst of one embodiment may comprise pores having a diameter of 5 to 200 nm and a volume of 0.1 to 3.0 cm³/g, and have BET specific surface area of 50 m²/g to 1000 m²/g, when the metal oxide is supported in a silica carrier.

This means that compared to catalysts prepared through coprecipitation and spray drying and having a secondary particle structure, pore size and volume are remarkably large, and BET specific surface area directly connected to the effective surface area capable of adsorbing ammonia gas and propylene gas is much broader.

Hereinafter, the catalyst of one embodiment will be explained in detail.

Structure of a Catalyst

The catalyst of one embodiment may have a structure comprising a silica carrier comprising second pores; an internal coating layer that continuously coats the wall surfaces of the second pores, and comprises metal oxide represented by Chemical Formula 1; and first pores positioned inside of the second pores, and occupying empty spaces except the internal coating layer.

Specifically, the catalyst of one embodiment may have an egg-shell structure.

For this purpose, a silica carrier comprising a non-porous core part; and a porous shell part positioned on the surface of the non-porous core, and comprising second pores; may be used.

More specifically, the porous shell comprises depressed parts and protruded parts of the surface, wherein the depressed parts may be formed by opening of the second pores toward the surface of the porous shell.

Thus, the catalyst of one embodiment may have a structure comprising a coating layer that continuously coats the depressed and protruded parts of the porous shell, and comprises metal oxide represented by the Chemical Formula 1; and first pores occupying empty spaces except the coating layer, in the depressed parts of the silica carrier. In the above structure, by controlling the properties of the second pores of the silica carrier, the properties of the first pores of the final catalyst may be controlled.

Specifically, a silica carrier in which the metal oxide is not supported may have D50 size of 20 to 400 μm; comprise second pores having diameter of 10 to 200 nm, and volume of 0.1 to 3 cm³/g; and have BET specific surface area of 50 to 1000 m²/g.

More specifically, a silica carrier on which the metal oxide is not supported may have D50 of 20 μm or more, 25 μm or more, 30 μm or more, 35 μm or more, 40 μm or more, or 43 μm or more, and 400 μm or less, 300 μm or less, 200 μm or less, 100 μm or less, 80 μm or less, or 70 μm or less.

And, the second pores included in a silica carrier in the which metal oxide is not supported may have diameter of 10 nm or more, 15 nm or more, or 20 nm or more, and 200 nm or less, 100 nm or less, 50 nm or less, 40 nm or less, or 30 nm or less; volume of 0.1 cm³/g or more, 0.3 cm³/g or more, 0.5 cm³/g or more, 0.7 cm³/g or more, 0.9 cm³/g or more, 1.1 cm³/g or more, 1.3 cm³/g or more, or 1.5 cm³/g or more, and 3 cm³/g or less, 2.8 cm³/g or less, 2.6 cm³/g or less, 2.4 cm³/g or less, 2.2 cm³/g or less, 2.0 cm³/g or less, 1.8 cm³/g or less, or 1.6 cm³/g or less.

And, a silica carrier in which the metal oxide is not supported may have BET specific surface area of 50 m²/g or more, 100 m²/g or more, 150 m²/g or more, 200 m²/g or more, or 250 m²/g or more, and 1000 m²/g or less, 900 m²/g or less, 800 m²/g or less, 700 m²/g or less, 600 m²/g or less, 500 m²/g or less, 400 m²/g or less, or 300 m²/g or less. In this case, when the metal oxide is supported in a silica carrier, the catalyst of one embodiment may have D50 size of 30 to 200 μm; comprise first pores having diameter of 5 nm to 200 nm, and volume of 0.1 to 3.0 cm³/g; and have BET specific surface area of 50 to 1000 m²/g.

More specifically, when the metal oxide is supported in a silica carrier, D50 particle diameter may be 30 μm or more, 35 μm or more, 40 μm or more, 45 μm or more, or 50 μm or more, and 200 μm or less, 190 μm or less, 180 μm or less, 170 μm or less, 160 μm or less, or 150 μm or less.

And, when the metal oxide is supported in a silica carrier, the first pores included in the catalyst of one embodiment may have diameter of 5 nm or more, 6 nm or more, 7 nm or more, 8 nm or more, or 10 nm or more, and 200 nm or less, 170 nm or less 150 nm or less, 130 nm or less or 100 nm or less; volume of 0.1 cm³/g or more, 0.2 cm³/g or more, 0.3 cm³/g or more, 0.4 cm³/g or more, 0.5 cm³/g or more or 0.6 cm³/g or more, and 3.0 cm³/g or less, 2.7 cm³/g or less, 2.5 cm³/g or less, 2.3 cm³/g or less or 2.0 cm³/g or less.

And, when the metal oxide is supported in a silica carrier, the catalyst of one embodiment may have BET specific surface area of 50 m²/g or more, 52 m²/g or more, 55 m²/g or more, 57 m²/g or more, or 60 m²/g or more, and 1000 m²/g or less, 900 m²/g or less, 800 m²/g or less, 700 m²/g or less, 600 m²/g or less, or 500 m²/g or less. For reference, the pore diameter and volume before and after supporting the metal oxide respectively mean average pore size and volume derived from BJH Formula through commonly known nitrogen adsorption/desorption test. The BET specific surface area before and after supporting the metal oxide may be calculated using commonly known BET measuring device.

The BET specific surface area of the catalyst of one embodiment, and diameter and volume of the first pores are improved compared to a catalyst having a secondary particle structure, thereby converting propylene with higher rate, and obtaining acrylonitrile with higher selectivity and yield.

In the above suggested ranges, as the diameter of the first pore is larger, the volume may increase and BET specific surface area may broaden. However, when the diameter and volume of the total catalyst are identical, as the diameter occupied by the first pores is larger, inflow of reactant propylene and discharge of product acrylonitrile may become easy and reaction properties may be improved, but volume occupied by the first pores may decrease and thus volume occupied by the metal oxide may relatively decrease, and thus, active sites may decrease and reactivity may be deteriorated.

Thus, considering the overall properties of the desired catalyst, the diameter and volume of the first pores, the diameter and BET specific surface area of the catalyst comprising the same, and the like may be controlled.

The properties of the first pores of the final catalyst may be also influenced by the amount of the metal precursor solution impregnated in the silica carrier, as well as by the properties of the second pores of the silica carrier. Detailed explanations thereof will be described later.

Composition of Metal Oxide

Meanwhile, even if a catalyst has the same structure as the catalyst of one embodiment, if the kind and content of the components constituting the metal oxide do not satisfy Chemical Formula 1, active sites formed may be insufficient for propylene ammoxidation or have excessively high density.

Thus, the kind and content of the components constituting the metal oxide should satisfy Chemical Formula 1.

Particularly, when the metal oxide is represented by Chemical Formula 1-1, due to synergistic effects of increasing movement speed of Fe, molybdenum, and lattice oxygen to increase conversion, increasing partial oxidation reaction property of propylene due to the formation of complex oxide of Co and molybdenum, and dispersing the active sites of complex oxide including K and molybdenum to increase selectivity of acrylonitrile, the activity in a propylene ammoxidation reaction may be further increased:

$$Mo_{12}Bi_aFe_bCo_cK_dO_x \qquad \text{Chemical Formula 1-1}$$

In the Chemical Formula 1-1,
a to d, and x are respectively fractions of each atom or atomic group, and a may be 0.1 to 5, specifically 0.1 to 2.0, b may be 0.1 to 5, specifically 0.5 to 3.0, c may be 0.01 to 10, specifically 1 to 10, d may be 0.01 to 2, specifically 0.01 to 1.0, and x may be 24 to 48, specifically 28 to 45.

Weight Ratio of Metal Oxide:Silica Carrier

The catalyst of one embodiment may comprise the metal oxide and the silica carrier at a weight ratio of 10:90 to 15:95, specifically 20:80 to 50:50, for example 15:85 to 35:65 (metal oxide:silica carrier).

Within this range, the catalyst of one embodiment may have high activity and high selectivity of acrylonitrile.

A Method for Preparing an Ammoxidation Catalyst for Propylene

According to another embodiment of the invention, there is provided a method for preparing the catalyst of one embodiment as explained above using impregnation.

As briefly explained above, the catalyst of one embodiment may be prepared by the processes of supporting a metal precursor solution in the silica carrier using impregnation, drying, and then, calcining. More specifically, the method for preparing the catalyst of one embodiment comprises the steps of:

preparing a first precursor solution comprising Mo precursor, preparing a second precursor solution comprising a Bi precursor, a Fe precursor, an A precursor (A=one or more elements of Ni, Mn, Co, Zn, Mg, Ca, and Ba), and a B precursor (B=one or more elements of Li, Na, K, Rb, and Cs), mixing the first and second precursor solutions such that the molar ratio of metals satisfies stoichiometric molar ratio of the following Chemical Formula 1, supporting the mixture of the first and second precursor solutions in a silica carrier, drying the silica carrier in which the mixture of the first and second precursor solutions is supported, and calcining the dried material:

$$Mo_{12}Bi_aFe_bA_cB_dC_eO_x \qquad \text{Chemical Formula 1}$$

in the Chemical Formula 1,
A is one or more elements of Ni, Mn, Co, Zn, Mg, Ca, and Ba,
B is one or more elements of Li, Na, K, Rb, and Cs,
C is one or more elements of Cr, W, B, Al, Ca, and V, and
a to e, and x are respectively fractions of each atom or atomic group, and a is 0.1 to 5, b is 0.1 to 5, c is 0.01 to 10, d is 0.01 to 2, e is 0 to 10, and x is 24 to 48.

A Preparation Process of the First Precursor Solution

The step of preparing a first precursor solution may comprise dissolving a Mo precursor in water of 20 to 80° C. to prepare a solution comprising water and Mo precursor.

In the step of preparing the first precursor solution, additives including citric acid, oxalic acid, or a mixture thereof may be used.

In the catalyst preparation process using coprecipitation and spray drying, these additives function as a strength control agent. However, in the above one embodiment, these additives make the first precursor solution transparent, enabling the preparation of a completely dissolved precursor mixture.

When adding the additives, the weight ratio of the molybdenum precursor and the additives may be controlled to satisfy 1:0.1 to 1:1, specifically 1:0.2 to 1:0.7, and within this range, solubility of the molybdenum precursor may be increased, but it is not limited thereto.

A Preparation Process of the Second Precursor Solution

Meanwhile, the second solution may comprise metal precursors, other than the Mo precursor included in the first precursor solution.

Specifically, the step of preparing the second precursor solution may include preparing a second precursor solution essentially comprising a Bi precursor, a Fe precursor, an A precursor, and a B precursor, and optionally, further comprising a C precursor (one or more elements of Cr, W, B, Al, Ca, and V), in water of 20 to 50° C.

More specifically, in the step of preparing the second precursor solution, considering the composition of metal oxide in the desired catalyst, the kinds of metal precursors other than Mo precursor may be selected.

For example, considering the composition of metal oxide satisfying the Chemical Formula 1-1, a second precursor solution comprising water, a Bi precursor, a Fe precursor, a Co precursor, and a K precursor may be prepared.

The processes of preparing the first and second precursor solutions are independent from each other, and the preparation sequence is not limited.

A Process for Supporting of a Mixture of the First and Second Precursor Solutions in a Carrier After mixing the first and second precursor solutions, the mixture may be supported on a silica carrier.

Wherein, the mixture of the first and second precursor solutions may be supported in the first pores in the silica carrier, by introducing the silica carrier comprising second pores as explained above in the mixture of the first and second precursor solutions.

Specifically, a silica carrier in which metal oxide is not supported may have D50 of 20 to 400 μm; and comprise second pores having a diameter of 10 to 200 nm, and a volume of 0.1 to 3 cm$^3$/g.

And, a silica carrier in which metal oxide is not supported may have BET specific surface area of 50 to 1000 m$^2$/g, specifically 100 to 700 m$^2$/g.

When using such a silica carrier, catalyst comprising first pores having a diameter of 5 nm to 100 nm, specifically 10 to 100 nm, and a volume of 0.2 to 3.0 cm$^3$/g, specifically 0.2 to 2.0 cm$^3$/g may be obtained.

And, as explained above, the BET specific surface area of the final catalyst may be 50 to 1000 m$^2$/g, specifically 60 to 500 m$^2$/g.

A Process of Drying a Carrier in which the Mixture of the First and Second Precursor Solutions is Supported The process of drying the silica carrier in which the mixture of the first and second precursor solutions is supported may comprise the steps of: first vacuum drying the silica carrier in which a mixture of the first and second precursor solutions is supported at 120 to 160 mbar, and second vacuum drying the first vacuum dried material at 30 to 50 mbar, to obtain a silica carrier in which a mixture of the first and second precursor solutions is supported.

Specifically, by conducting the first vacuum drying at 60 to 80° C. for 1 to 2 hours, and conducting the second vacuum drying at 80 to 100° C. for 15 to 45 minutes, the solvent (namely, water) may be removed, and only the first and second precursors may remain on the wall surfaces of the first pores.

Although the second vacuum dried material may be immediately calcined, by third drying at atmospheric pressure, even the solvent (namely, water) remaining after the second vacuum drying may be effectively removed.

Specifically, the third drying may be conducted at 100 to 150° C. for 20 to 30 hours.

However, these are no more than examples, and drying conditions are not specifically limited as long as a carrier in which the first and second precursors are supported may be obtained.

Final Calcination Process

Finally, the dried material, namely, a carrier in which the first and second precursors are supported may be calcined at 500 to 700° C. for 2 to 5 hours to finally obtain a catalyst.

However, the drying and calcinations conditions are no more than examples, and any conditions may be sufficient as long as the solvents may be sufficiently removed from the internal pores of the carrier, and metal precursor may be oxidized.

Ammoxidation Method for Propylene

According to yet another embodiment of the invention, there is provided a method for ammoxidation of propylene, comprising a step of reacting propylene and ammonia in the presence of the catalyst of the one embodiment, as explained above, in a reactor.

The catalyst of one embodiment has high activity and high temperature stability, and may be used for a propylene ammoxidation reaction to increase conversion of propylene, selectivity, and yield of acrylonitrile.

For the details other than the catalyst of one embodiment, matters commonly known in the art may be referred to, and the detailed explanations thereof are omitted.

Hereinafter, embodiments of the invention will be explained in more detail in the following examples. However, these examples are presented only as the illustrations of the invention, and the scope of the invention is not limited thereby.

EXAMPLES

Example 1

(1) A Preparation Process of a Precursor Solution

In distilled water at 60° C., 10.592 g of a Mo precursor ((NH$_4$)$_6$Mo$_7$O$_{24}$) and 3.18 g of citric acid were introduced, and mixed to prepared a Mo precursor solution.

Separately, in distilled water at room temperature, 1.819 g of a Bi precursor (Bi(NO$_3$)$_3$·5H$_2$O), 9.488 g of a Co precursor (Co(NO$_3$)$_2$·6H$_2$O), 2.990 g of a Fe precursor (Fe(NO$_3$)$_2$·9H$_2$O), and 0.354 g of a K precursor (KNO$_3$) were introduced, and 2.16 g of nitric acid (HNO$_3$) was added, and then, they were mixed to prepare a mixed solution of Bi, Fe, Co, and K precursors.

The Mo precursor solution; and the mixed solution of Bi, Fe, Co, and K precursors were mixed to complete a mixed solution of Mo, Bi, Fe, Co, and K precursors.

In the mixed solution of precursors, the total amount of distilled water was 54.07 g.

(2) A Process of Supporting a Precursor Solution in a Silica Carrier (Using Impregnation)

Silica (SiO$_2$, SP948, Grace) particles having D50 particle diameter of 55 μm, internal pore size of 24.4 nm, BJH pore volume according to nitrogen adsorption of 1.58 cm³/g, and BET specific surface area of 283 m²/g were used as a carrier.

In the mixed solution of Mo, Bi, Fe, Co, and K precursors, the silica carrier was introduced, and the solution was stirred sequentially at room temperature and 80° C., respectively for 2 hours, such that the mixed solution of Mo, Bi, Fe, Ni, Co, and K precursors was sufficiently supported in the internal pores of the silica carrier.

(3) Processes of Drying and Calcination of a Silica Carrier in which a Precursor Solution is Supported Thereafter, the silica carrier in which the mixed solution of Bi, Fe, Co, and K precursors was supported was recovered and introduced in a rotary vacuum dryer, and then, first vacuum dried under pressure of 140 mbar and temperature of 70° C. for 1 hour and 40 minutes, and second vacuum dried under pressure of 40 mbar and temperature of 90° C. for 30 minutes.

The second vacuum dried material was recovered and introduced into an oven, and dried for a third time under atmospheric pressure and temperature of 110° C. for 24 hours, and then, while maintaining a temperature of 580° C. in a box calcination furnace of air atmosphere, heat treated for 3 hours to finally obtain a catalyst of Example 1.

(4) A Process of Propylene Ammoxidation

In a tubular reactor having an inner diameter of ⅜ inches, 0.05 g of quartz wool was charged and 0.2 g of the catalyst of Example 1 was charged in the reactor.

The internal pressure of the reactor charged with quartz wool and catalyst was maintained at atmospheric pressure (1 atm), and while raising the internal temperature of the reactor at 10° C./min, nitrogen and ammonia gas were flowed as pretreatment. After the internal temperature of the reactor reached 400° C. at which an ammoxidation reaction can be progressed, it was maintained under reducing gas atmosphere for 15 minutes so as to achieve sufficient pretreatment.

While supplying air together with reactants of propylene and ammonia in the pretreated reactor, an ammoxidation process of propylene was conducted. Wherein, the amounts of the reactants supplied were such that a volume ratio became propylene:ammonia:air=0.8:1.2:8, and the total weight hourly space velocity (WHSV) of propylene, ammonia and air became 1.54 $h^{-1}$.

After the ammoxidation reaction was completed, the product was recovered, and in order to confirm whether acrylonitrile was sufficiently produced, it was analyzed using various apparatuses.

The analysis method, analysis results, and the like will be explained in detail in Experimental Examples below.

Examples 2 to 7

(1) A Preparation Process of a Catalyst (Using Impregnation)

Each catalyst of Examples 2 to 7 was prepared by the same method as Example 1, except that a precursor solution was prepared according to the composition described in the following Table 1, and a silica carrier described in the following Table 2 was used.

(2) An Ammoxidation Process of Propylene

An ammoxidation process of propylene was conducted using each catalyst of Examples 2 to 7 instead of Example 1, and then, the product was recovered, and analyzed by the same method as Example 1.

Comparative Example 1

(1) A Preparation Process of a Catalyst (Coprecipitation and Spray Drying)

First, in distilled water at 60° C., 10.592 g of a Mo precursor ($(NH_4)_6Mo_7O_{24}$) and 3.18 g of citric acid were introduced and mixed to prepare a Mo precursor solution.

Separately, in distilled water at room temperature, 1.819 g of a Bi precursor ($Bi(NO_3)_3 \cdot 5H_2O$), 9.488 g of a Co precursor ($Co(NO_3)_2 \cdot 6H_2O$), 2.990 g of a Fe precursor ($Fe(NO_3)_2 \cdot 9H_2O$), and 0.354 g of a K precursor ($KNO_3$) were introduced, and 0.83 g of nitric acid ($HNO_3$) was added, and then, they were mixed to prepare a mixed solution of Bi, Fe, Co, and K precursors.

The Mo precursor solution; and the mixed solution of Bi, Fe, Co, and K precursors were mixed, and 22.530 g of silica sol (LUDOX AS 40, solid content: 40%) was added thereto, and the mixture was stirred, and then, spray dried under conditions of 120° C. (inlet) and 230° C. (outlet) using a disk-type spray dryer.

The obtained powders were calcined at 580° C. for 3 hours to finally obtain a catalyst of Comparative Example 1.

(2) An Ammoxidation Process of Propylene

An ammoxidation process of propylene was conducted by the same method as Example 1, except that the catalyst of Comparative Example 1 was used instead of the catalyst of Example 1.

After the ammoxidation reaction of Comparative Example 1 was finished, the product was recovered, and analyzed by the same method as Example 1.

Comparative Example 2

(1) A Preparation Process of a Catalyst (Coprecipitation and Spray Drying)

A catalyst of Comparative Example 2 was prepared by the same method as Comparative Example 1, except that a precursor solution was prepared according to the composition described in the following Table 1, and a silica carrier described in the following Table 2 was used.

(2) An Ammoxidation Process of Propylene

An ammoxidation process of propylene was conducted using the catalyst of Comparative Example 2 instead of the catalyst of Comparative Example 1, and then, the product was recovered and analyzed by the same method as Comparative Example 1.

Comparative Example 3

(1) A Preparation Process of a Catalyst (Coprecipitation and Spray Drying)

A catalyst of Comparative Example 3 was prepared by the same method as Example 1, except that a precursor solution was prepared according to the composition described in the following Table 1, and a silica carrier described in the following Table 2 was used.

(2) An Ammoxidation Process of Propylene

An ammoxidation process of propylene was conducted using the catalyst of Comparative Example 3 instead of the catalyst of Example 1, and then, the product was recovered and analyzed by the same method as Example 1.

Comparative Example 4

(1) A Preparation Process of a Catalyst (Coprecipitation and Spray Drying)

First, in distilled water at 60° C., 10.592 g of a Mo precursor $((NH_4)_6Mo_7O_{24})$ and 3.18 g of citric acid were introduced and mixed to prepare a Mo precursor solution.

Separately, in distilled water at room temperature, 1.091 g of a Bi precursor $(Bi(NO_3)_3 \cdot 5H_2O)$, 4.365 g of a Co precursor $(Co(NO_3)_2 \cdot 6H_2O)$, 3.636 g of a Fe precursor $(Fe(NO_3)_2 \cdot 9H_2O)$, 2.908 g of a Ni precursor $(Ni(NO_3)_2 \cdot 6H_2O)$, 0.045 g of a K precursor $(KNO_3)$, 1.954 g of a Ce precursor $(Ce(NO_3)_3 \cdot 6H_2O)$, 2.564 g of a Mg precursor $(Mg(NO_3)_2 \cdot 6H_2O)$, and 0.037 g of a Rb precursor $(RbNO_3)$ were introduced, and 0.83 g of nitric acid $(HNO_3)$ was added, and they were mixed to prepare a mixed solution of Bi, Co, Fe, Ni, K, Ce, Mg, and Rb precursors.

The Mo precursor solution; and the mixed solution of Bi, Co, Fe, Ni, K, Ce, Mg, and Rb precursors were mixed to complete a mixed solution of Mo, Bi, Fe, Co, and K precursors.

In the mixed solution of precursors, the total amount of distilled water was 27.33 g.

(2) An Ammoxidation Process of Propylene

An ammoxidation process of propylene was conducted using the catalyst of Comparative Example 4 instead of the catalyst of Example 1, and then, the product was recovered and analyzed by the same method as Example 1.

TABLE 1

|  | Mo precursor solution | | Heterogeneous metal precursor solution | | | | | | |
| --- | --- | --- | --- | --- | --- | --- | --- | --- | --- |
|  | Citric acid | Mo | Bi | Co | Fe | K | nitric acid | Distilled water | $SiO_2$ |
| Example1 | 3.18 | 10.592 | 1.819 | 9.488 | 2.990 | 0.354 | 2.16 | 54.07 | 27.04 |
| Example2 | 3.18 | 10.592 | 2.425 | 6.403 | 2.020 | 0.177 | 2.03 | 50.68 | 25.338 |
| Example3 | 3.18 | 10.592 | 1.989 | 9.313 | 1.616 | 0.076 | 2.10 | 52.51 | 26.257 |
| Example4 | 3.18 | 10.592 | 2.425 | 6.403 | 2.020 | 0.177 | 4.73 | 118.25 | 59.123 |
| Example5 | 3.18 | 10.592 | 2.425 | 6.403 | 2.020 | 0.177 | 3.19 | 79.63 | 39.817 |
| Example6 | 3.18 | 10.592 | 1.819 | 9.488 | 2.990 | 0.354 | 1.25 | 31.37 | 15.686 |
| Example7 | 3.18 | 10.592 | 1.819 | 9.488 | 2.990 | 0.354 | 0.83 | 20.65 | 10.323 |
| Comparative Example1 | 3.18 | 10.592 | 1.819 | 9.488 | 2.990 | 0.354 | 0.83 | 20.65 | 22.530 (40% Silica sol) |
| Comparative Example2 | 3.18 | 10.592 | 2.425 | 6.403 | 2.020 | 0.177 | 2.03 | 50.68 | 63.346 (40% Silica sol) |
| Comparative Example3 | 1.06 | 3.531 | 19.403 |  |  | 1.415 | 2.60 | 64.95 | 32.477 |

In Table 1, Mo is $(NH_4)_6Mo_7O_{24}$, Bi is $Bi(NO_3)_3 \cdot 5H_2O$, Co is $Co(NO_3)_2 \cdot 6H_2O$, Fe is $Fe(NO_3)_2 \cdot 9H_2O$, and K is $KNO_3$. And, the omitted unit is g.

Meanwhile, Comparative Example 4 wherein many materials were added to a heterogeneous metal precursor solution was omitted in the Table 1 for convenience.

TABLE 2

|  | | Catalyst construction | | |
| --- | --- | --- | --- | --- |
|  | Preparation method | Content and composition of active material(metal oxide) | Carrier content | Carrier Product name |
| Example 1 | Impreg. | 25 wt % $(Mo_{12}Bi_{0.75}Fe_{1.48}Co_{6.52}K_{0.7}O_x)$ | 75 wt % | SP948 (Grace) |
| Example 2 | Impreg. | 25 wt % $(Mo_{12}Bi_{1.0}Fe_{1.0}Co_{4.4}K_{0.35}O_x)$ | 75 wt % | SP948 (Grace) |
| Example 3 | Impreg. | 25 wt % $(Mo_{12}Bi_{0.82}Fe_{0.8}Co_{6.4}K_{0.15}O_x)$ | 75 wt % | SP948 (Grace) |
| Example 4 | Impreg. | 12.5 wt % $(Mo_{12}Bi_{1.0}Fe_{1.0}Co_{4.4}K_{0.35}O_x)$ | 87.5 wt % | SP948 (Grace) |
| Example 5 | Impreg. | 17.5 wt % $(Mo_{12}Bi_{1.0}Fe_{1.0}Co_{4.4}K_{0.35}O_x)$ | 82.5 wt % | SP948 (Grace) |
| Example 6 | Impreg. | 35 wt % $(Mo_{12}Bi_{0.75}Fe_{1.48}Co_{6.52}K_{0.7}O_x)$ | 65 wt % | SP948 (Grace) |
| Example 7 | Impreg. | 45 wt % $(Mo_{12}Bi_{0.75}Fe_{1.48}Co_{6.52}K_{0.7}O_x)$ | 55 wt % | SP948 (Grace) |
| Comp. Example 1 | Coprecip. | 50 wt % $(Mo_{12}Bi_{0.75}Fe_{1.48}Co_{6.52}K_{0.7}O_x)$ | 50 wt % | LUDOX_AS40 (Grace) |
| Comp. Example 2 | Coprecip. | 25 wt % $(Mo_{12}Bi_{1.0}Fe_{1.0}Co_{4.4}K_{0.35}O_x)$ | 75 wt % | LUDOX_AS40 (Grace) |
| Comp. Example 3 | Impreg. | 25 wt % $(Bi_2O_{3.3}MoO_3)$ | 75 wt % | SP948 (Grace) |
| Comp. Example 4 | Impreg. | 25 wt % $(Mo_{12}Bi_{0.45}Ce_{0.90}Fe_{1.8}Ni_{2.0}Co_{3.0}Mg_{2.0}K_{0.09}Rb_{0.05}O_n)$ | 75 wt % | SP948 (Grace) |

Experimental Example 1: Catalyst Analysis

According to the following analysis method, each catalyst of Examples 1 to 7 and Comparative Examples 1 to 4 was analyzed:
BET Specific Surface Area:

Using BET specific surface area measuring device (Manufacturing company: BEL Japan, Device name: BEL-SORP_Mini), specific surface area was evaluated from nitrogen gas adsorption amount under liquid nitrogen temperature (77K), and the results were shown in the following Table 3.
Pore Size and Volume:

Using BET specific surface area measuring device (Manufacturing company: BEL Japan, Device name: BEL-SORP_Mini), pore size and volume were measured from BJH Formula using adsorption amount measured until relative pressure (P/PO) of 1 under liquid nitrogen temperature (77K), and desorption amount measured until 0.03, and shown in Table 3.
Catalyst Composition:

The composition of a catalyst may be measured by ICP method. After weighing 0.01 g of a catalyst in a corning tube, 3 ml of nitric acid and 0.1 ml of hydrofluoric acid were added to the same, followed by elution in a ultra-sonicator for more than 1 hour. 1 ml of a saturated boric acid solution was introduced, and 50 ml of triple distilled water was added to prepare a solution, and then, using CIP-OES quantitative analysis apparatus (PerkinElmer, OPTIMA 8300DV), quantitative analysis of each component was conducted. And, the composition and ratio were shown in Table 3.
D50:

Using laser diffraction type particle size analyzer (Microtrac, S3500), after sonication under 30 watt for 1 minute after sample introduction, volume based D50 was derived through particle size analysis and shown in Table 3.

favorable for the preparation of a catalyst having large pore size and volume, and thus wide BET specific surface area.

Wherein, since the catalysts of Comparative Example 1 and 2 were prepared through coprecipitation and spray drying, they scarcely include pores, and have relatively narrow BET specific surface areas. On the contrary, since the catalysts of Examples 1 to 7 were prepared using impregnation, they include a plurality of large pores, and have relatively wide BET specific surface area.

As representative examples, for each catalyst of Example 1 and Comparative Example 1, using SEM: Hitachi S-4800 Scanning Electron Microscope, the SEM (Scanning Electron Microscope) image of 100 magnification was obtained, and each SEM image was shown in FIG. 3(Example 1) and FIG. 4(Comparative Example 1).

Figure 4:
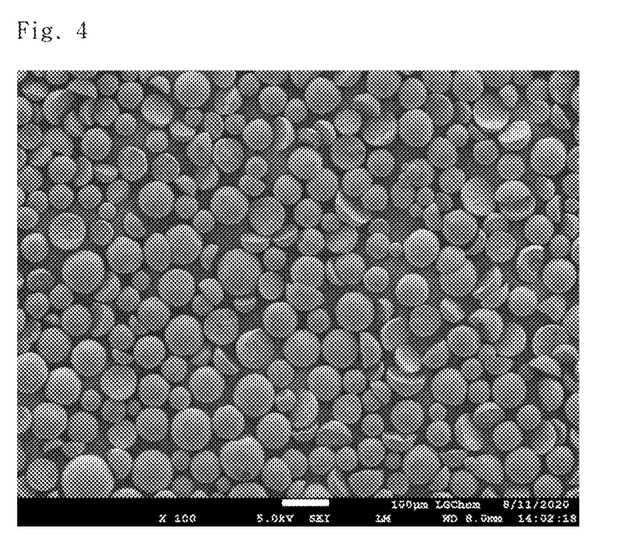
FIG. 4 is the SEM image (100 magnification) of the catalyst of Comparative Example 1.

Specifically, it can be seen that the catalyst of Comparative Example 1 generally has a particle diameter of 28 to 50 μm, and has a secondary particle structure wherein metal oxide particles are uniformly distributed inside and outside, but scarcely includes internal pores.

Figure 3:
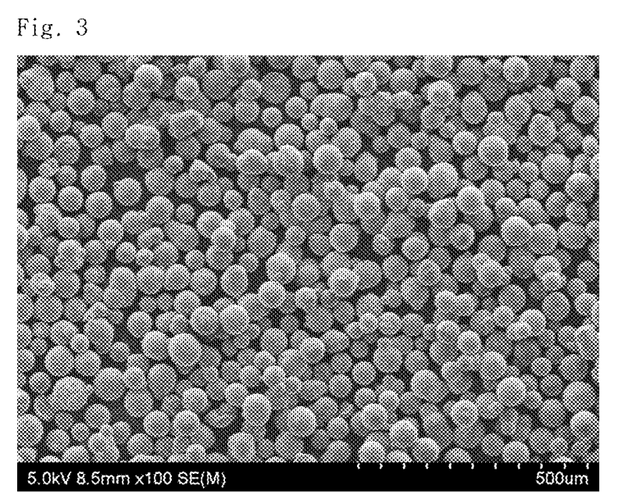
FIG. 3 is the SEM image (100 magnification) of the catalyst of Example 1.

On the contrary, it can be seen that the catalyst of Example 1 generally has a particle diameter of 50 to 112 μm, a metal oxide coating layer that continuously coats the porous shell part of the silica carrier is formed, and a plurality of large empty spaces (pores) except the coating layer exist in the porous shell part of the silica carrier.

Meanwhile, the catalyst of Comparative Example 3, although prepared using impregnation, the pore size and volume, and BET specific surface area are equivalent to those of Comparative Examples 1 and 2.

It means that by the influence of metal oxide comprising only Mo and Bi as active metals, a catalyst having relatively small pore size and volume, and narrow BET specific surface area was prepared. Since the catalyst of Comparative Example 4 was prepared by impregnation and comprises a plurality of heterogeneous metals as well as Mo and Bi as

TABLE 3

| | Preparation method | Content and composition of active material(metal oxide) | Catalyst form | Catalyst BET ($m^2/g$) | Pore size in catalyst (nm) | Pore volume in catalyst ($cm^3/g$) | D50 (μm) |
|---|---|---|---|---|---|---|---|
| Ex. 1 | Impreg. | 25 wt % ($Mo_{12}Bi_{0.75}Fe_{1.48}Co_{6.52}K_{0.7}O_x$) | Egg-shell | 105 | 28.1 | 0.75 | 55 |
| Ex. 2 | Impreg. | 25 wt % ($Mo_{12}Bi_{1.0}Fe_{1.0}Co_{4.4}K_{0.35}O_x$) | Egg-shell | 125 | 24.4 | 0.84 | 112 |
| Ex. 3 | Impreg. | 25 wt % ($Mo_{12}Bi_{0.82}Fe_{0.8}Co_{6.4}K_{0.15}O_x$) | Egg-shell | 128 | 24.7 | 0.92 | 57 |
| Ex. 4 | Impreg. | 12.5 wt % ($Mo_{12}Bi_{1.0}Fe_{1.0}Co_{4.4}K_{0.35}O_x$) | Egg-shell | 234 | 28.3 | 1.23 | 62 |
| Ex. 5 | Impreg. | 17.5 wt % ($Mo_{12}Bi_{1.0}Fe_{1.0}Co_{4.4}K_{0.35}O_x$) | Egg-shell | 178 | 25.4 | 1.15 | 59 |
| Ex. 6 | Impreg. | $Mo_{12}Bi_{0.75}Fe_{1.48}Co_{6.52}K_{0.7}O_x$: 35 wt % | Egg-shell | 106 | 22.6 | 0.75 | 52 |
| Ex. 7 | Impreg. | $Mo_{12}Bi_{0.75}Fe_{1.48}Co_{6.52}K_{0.7}O_x$: 45 wt % | Egg-shell | 68 | 15.5 | 0.62 | 50 |
| Comp. Ex. 1 | Coprecip. | 35 wt % ($Mo_{12}Bi_{0.75}Fe_{1.48}Co_{6.52}K_{0.7}O_x$) | Uniform | 25 | 8 | 0.15 | 30 |
| Comp. Ex. 2 | Coprecip. | 45 wt % ($Mo_{12}Bi_{0.75}Fe_{1.48}Co_{6.52}K_{0.7}O_x$) | Uniform | 31 | 9 | 0.18 | 50 |
| Comp. Ex. 3 | Impreg. | 25 wt % ($Bi_2O_{3.3}MoO_3$) | Egg-shell | 45 | 12.3 | 0.06 | 28 |
| Comp. Ex. 4 | Impreg. | 25 wt % ($Mo_{12}Bi_{0.45}Ce_{0.90}Fe_{1.8}Ni_{2.0}Co_{3.0}Mg_{2.0}K_{0.09}Rb_{0.05}O_n$) | Egg-shell | 106 | 24.7 | 0.94 | 43 |

According to Table 3, it can be seen that compared to coprecipitation and spray drying used for preparing the catalysts of Comparative Examples 1 and 2, impregnation used for preparing the catalysts of Examples 1 to 7 is active metals, it has BET specific surface area equivalent to those of Examples 1 to 7. However, in order to evaluate the influence by the active metals, there is a need to additionally analyze the ammoxidation product.

Experimental Example 2: Analysis of Ammoxidation Product

Using Gas chromatography (Manufacturing company: Agilent Device name: HP 6890 N) equipped with FID (Flame Ionization Detector and TCD (Thermal conductivity detector), each ammoxidation product of Examples and Comparative Examples was analyzed.

Specifically, with FID, products including ethylene, hydrogen cyanide, acetaldehyde, acetonitrile, acrylonitrile, and the like were analyzed, and with TCD, gas products including $NH_3$, $O_2$, CO, $CO_2$, and the like and unreacted propylene were analyzed, thus calculating the mole number of reacted propylene and the mole number of ammoxidation product in Examples and Comparative Examples.

The analysis results and the mole number of supplied propylene were substituted in the following Formulas 1, 2 and 3, thus calculating conversion of propylene, selectivity and yield of acrylonitrile, which is the ammoxidation reaction product of propylene, and the calculation values were described in the following Table 4:

Conversion of propylene (%)=100*(mole number of ammoxidation of reacted propylene)/(mole number of supplied propylene)   Formula 1

Selectivity of acrylonitrile (%)=100*(mole number of produced acrylonitrile)/(mole number of reacted propylene)   Formula 2

Yield of acrylonitrile (%)=100*(mole number of produced acrylonitrile)/(mole number of supplied propylene)   Formula 3 effective surface area capable of participating in the reaction is small.

Practically, it is confirmed that during the reaction using the catalyst of Comparative Example 3, conversion of propylene is 10%, and yield of acrylonitrile is less than 6%.

Since the catalyst of Comparative Example 4 is prepared by impregnation, and includes plural heterogeneous metals as well as Mo and Bi as active metals, the effective surface area capable of participating reactions is large.

Nevertheless, during the reaction using the catalyst of Comparative Example 4, conversion of propylene is less than 55%, selectivity to acrylonitrile is less than 70%, and the yield is less than 35%. It is assumed that since Ce, Fe, Ni, Co, Mg, K, and Rb as well as Mo and Bi were included as active metals, and particularly Ce is included, active sites of excessively high density was formed.

On the contrary, the catalysts of Examples 1 to 7 include pores of large size and volume, and have large effective surface area capable of participating in reactions.

Practically, it is confirmed that during the reactions using the catalysts of Examples 1 to 7, conversion of propylene is remarkably increased to 60% or more, and yield of acrylonitrile is remarkably increased to 45% or more.

Thus, it can be seen that catalysts capable of improving conversion of propylene and yield of acrylonitrile during the ammoxidation reaction of propylene are those wherein the composition of metal oxide satisfies the above explained Chemical Formula 1, and when the metal oxide is supported in a silica carrier, pores having particle diameter of 2 to 200

TABLE 4

| | | | Analysis results of ammoxidation product of propylene | | |
|---|---|---|---|---|---|
| | Preparation method | Content and composition of active material (metal oxide) | Convers. of propylene (%) | Selectivity of acrylonitrile (%) | Yield of acrylonitrile (%) |
| Ex. 1 | Impreg. | 25 wt % ($Mo_{12}Bi_{0.75}Fe_{1.48}Co_{6.52}K_{0.7}O_x$) | 61 | 76 | 47 |
| Ex. 2 | Impreg. | 25 wt % ($Mo_{12}Bi_{1.0}Fe_{1.0}Co_{4.4}K_{0.35}O_x$) | 79 | 79 | 63 |
| Ex. 3 | Impreg. | 25 wt % ($Mo_{12}Bi_{0.82}Fe_{0.8}Co_{6.4}K_{0.15}O_x$) | 82 | 86 | 71 |
| Ex. 4 | Impreg. | 12.5 wt % ($Mo_{12}B_{1.0}Fe_{1.0}Co_{4.4}K_{0.35}O_x$) | 61 | 80 | 49 |
| Ex. 5 | Impreg. | 17.5 wt % ($Mo_{12}Bi_{1.0}Fe_{1.0}Co_{4.4}K_{0.35}O_x$) | 73 | 82 | 60 |
| Ex. 6 | Impreg. | 35 wt % ($Mo_{12}Bi_{0.75}Fe_{1.48}Co_{6.52}K_{0.7}O_x$) | 68 | 72 | 49 |
| Ex. 7 | Impreg. | 45 wt % ($Mo_{12}Bi_{0.75}Fe_{1.48}Co_{6.52}K_{0.7}O_x$) | 65 | 69 | 45 |
| Comp. Ex. 1 | Coprecip. | 50 wt % ($Mo_{12}Bi_{0.75}Fe_{1.48}Co_{6.52}K_{0.7}O_x$) | 25 | 37 | 9 |
| Comp. Ex. 2 | Coprecip. | 25 wt % ($Mo_{12}Bi_{1.0}Fe_{1.0}Co_{4.4}K_{0.35}O_x$) | 48 | 69 | 33 |
| Comp. Ex. 3 | Impreg. | 25 wt % ($Bi_2O_{3.3}MoO_3$) | 10 | 54 | 5.4 |
| Comp. Ex. 4 | Impreg. | 25 wt % ($Mo_{12}Bi_{0.45}Ce_{0.90}Fe_{1.8}Ni_{2.0}Co_{3.0}Mg_{2.0}K_{0.09}Rb_{0.05}O_n$) | 53 | 64 | 34 |

Since the catalysts of Comparative Examples 1 and 2 were prepared through coprecipitation and spray drying, internal pores are scarcely included, and thus, parts capable of participating in reactions are limited to the external surface part.

Practically, it is confirmed that during the reaction using when the catalyst of Comparative Examples 1 and 2, conversion of propylene is less than 50%, and yield of acrylonitrile is less than 35%.

Meanwhile, the catalyst of Comparative Example 3, although prepared by impregnation, due to the influence of metal oxide comprising only Mo and Bi as active metals, the nm and volume of 0.1 to 3.0 $cm^3/g$ are included, and BET specific surface area is 50 $m^2/g$ to 1000 $m^2/g$.

Furthermore, it is also possible to further improve conversion of propylene and yield of acrylonitrile, by controlling the content and composition of metal oxide, referring to the catalysts of Examples 1 to 7.

The invention claimed is:

1. An ammoxidation catalyst for propylene in which metal oxide represented by Chemical Formula 1 is supported on a silica carrier,
    wherein the catalyst comprises pores having a diameter of 5 to 200 nm, a pore volume of 0.1 to 3.0 $cm^3/g$, and wherein the catalyst has BET specific surface area of 50 m²/g to 1000 m²/g:

$$Mo_{12}Bi_aFe_bA_cB_dC_eO_x \qquad \text{Chemical Formula 1}$$

wherein in Chemical Formula 1,
A is one or more elements of Ni, Mn, Co, Zn, Mg, Ca, and Ba,
B is one or more elements of Li, Na, K, Rb, and Cs,
C is one or more elements of Cr, W, B, Al, Ca, and V, and
a to e, and x are respectively fractions of each atom or atomic group, wherein a is 0.1 to 5, b is 0.1 to 5, c is 0.01 to 10, d is 0.01 to 2, e is 0 to 10, and x is 24 to 48.

2. The ammoxidation catalyst for propylene according to claim 1, wherein the catalyst comprises
a silica carrier comprising second pores;
an internal coating layer that coats wall surfaces of the second pores, and comprises the metal oxide represented by the Chemical Formula 1; and
first pores positioned inside of the second pores, and occupying empty spaces except the internal coating layer.

3. The ammoxidation catalyst for propylene according to claim 1, wherein the catalyst has BET specific surface area of 60 to 500 m²/g.

4. The ammoxidation catalyst for propylene according to claim 1, wherein the catalyst comprises pores having a diameter of 10 to 100 nm.

5. The ammoxidation catalyst for propylene according to claim 1, wherein the catalyst comprises pores having a volume of 0.6 to 2.0 cm³/g.

6. The ammoxidation catalyst for propylene according to claim 1, wherein the catalyst has a D50 particle diameter of 50 to 200 μm.

7. The ammoxidation catalyst for propylene according to claim 1, wherein the metal oxide is represented by Chemical Formula 1-1:

$$Mo_{12}Bi_aFe_bCo_cK_dO_x \qquad \text{Chemical Formula 1-1}$$

wherein in Chemical Formula 1-1, a is 0.1 to 5, b is 0.1 to 5, c is 0.01 to 10, d is 0.01 to 2, and x is 24 to 48.

8. The ammoxidation catalyst for propylene according to claim 1, wherein a weight ratio of the metal oxide and the silica carrier is 15:85 to 35:65.

9. A method for preparing the ammoxidation catalyst for propylene according to claim 1, comprising:
preparing a first precursor solution comprising a Mo precursor,
preparing a second precursor solution comprising a Bi precursor, a Fe precursor, an A precursor, wherein A is one or more elements of Ni, Mn, Co, Zn, Mg, Ca, and Ba, and a B precursor, wherein B is one or more elements of Li, Na, K, Rb, and Cs, or a second precursor solution comprising a Bi precursor, a Fe precursor, an A precursor, wherein A is one or more elements of Ni, Mn, Co, Zn, Mg, Ca, and Ba, a B precursor, wherein B is one or more elements of Li, Na, K, Rb, and Cs, and a C precursor, wherein C is one or more elements of Cr, W, B, Al, Ca, and V,
mixing the first and second precursor solutions such that a molar ratio of metals satisfies stoichiometric molar ratio of Chemical Formula 1,
supporting the mixture of the first and second precursor solutions on a silica carrier,
drying the silica carrier in which the mixture of the first and second precursor solutions is supported, and
calcining the dried material:

$$Mo_{12}Bi_aFe_bA_cB_dC_eO_x \qquad \text{Chemical Formula 1}$$

wherein in Chemical Formula 1,
A is one or more elements of Ni, Mn, Co, Zn, Mg, Ca, and Ba,
B is one or more elements of Li, Na, K, Rb, and Cs,
C is one or more elements of Cr, W, B, Al, Ca, and V, and
a to e, and x are respectively fractions of each atom or atomic group, wherein a is 0.1 to 5, b is 0.1 to 5, c is 0.01 to 10, d is 0.01 to 2, e is 0 to 10, and x is 24 to 48.

10. The method according to claim 9, wherein the second precursor solution further comprising a C precursor, wherein C is one or more elements of Cr, W, B, Al, Ca, and V.

11. The method according to claim 9, wherein the second precursor solution comprises a Bi precursor, a Fe precursor, a Co precursor, and a K precursor.

12. The method according to claim 9, wherein the silica carrier comprises pores having a diameter of 10 to 200 nm and a volume of 0.1 to 3 cm³/g.

13. The method according to claim 9, wherein the silica carrier has BET specific surface area of 50 m²/g to 1000 m²/g.

14. The method according to claim 9, wherein drying the silica carrier in which a mixture of the first and second precursor solutions is supported comprises:
a first vacuum drying of the silica carrier in which a mixture of the first and second precursor solutions is supported at 120 to 160 mbar, and
a second vacuum drying of the first vacuum dried material at 30 to 50 mbar, to obtain a silica carrier in which a mixture of the first and second precursor solutions is supported.

15. The method according to claim 14, wherein the first vacuum drying is conducted at 60 to 80° C.

16. The method according to claim 14, wherein the second vacuum drying is conducted at 80 to 100° C.

17. The method according to claim 14, further comprising a third drying the second vacuum dried material at atmospheric pressure.

18. The method according to claim 17, wherein the third drying is conducted at 100 to 150° C.

19. The method according to claim 9, wherein the calcining of the dried material is conducted at 500 to 700° C.

20. A method for ammoxidation of propylene, comprising reacting propylene and ammonia in the presence of the catalyst of claim 1, in a reactor.

* * * * *